(12) United States Patent
Madson (10) Patent No.: US 9,726,671 B2
(45) Date of Patent: Aug. 8, 2017

(54) METHOD OF DISCERNING SUBSTITUTION OF CARBOHYDRATE ESTERS

(71) Applicant: BIOLOGISTICS LLC, Ames, IA (US)

(72) Inventor: Michael Madson, Ames, IA (US)

(73) Assignee: BIOLOGISTICS LLC, Ames, IA (US)

( * ) Notice: Subject to any disclaimer, the term of this patent is extended or adjusted under 35 U.S.C. 154(b) by 275 days.

(21) Appl. No.: 14/534,546

(22) Filed: Nov. 6, 2014

(65) Prior Publication Data

US 2015/0064793 A1 Mar. 5, 2015

Related U.S. Application Data

(63) Continuation-in-part of application No. 13/426,891, filed on Mar. 22, 2012, now Pat. No. 8,993,226.

(60) Provisional application No. 61/513,921, filed on Aug. 1, 2011.

(51) Int. Cl.
| | |
|---|---|
| *G01N 33/00* | (2006.01) |
| *G01N 37/00* | (2006.01) |
| *G01N 30/72* | (2006.01) |
| *G01N 33/58* | (2006.01) |
| *G01N 33/04* | (2006.01) |
| *G01N 30/88* | (2006.01) |
| *G01N 30/60* | (2006.01) |
| *G01N 30/96* | (2006.01) |

(52) U.S. Cl.
CPC .............. *G01N 33/58* (2013.01); *G01N 30/88* (2013.01); *G01N 33/04* (2013.01); *G01N 30/6091* (2013.01); *G01N 30/96* (2013.01); *G01N 2030/8836* (2013.01)

(58) Field of Classification Search
None
See application file for complete search history.

(56) References Cited

U.S. PATENT DOCUMENTS

| | | | |
|---|---|---|---|
| 2007/0105179 A1 | 5/2007 | Madson | |
| 2007/0224620 A1* | 9/2007 | Hartzell | ........... G01N 33/54306 435/6.12 |
| 2009/0104603 A1* | 4/2009 | Satomaa | ................. C08B 37/00 435/6.14 |

OTHER PUBLICATIONS

Wu et al. Journal of Proteome Research 2011, 10, 856-868.*
D.J. Harvey / J. Chromatogr. B 879 (2011) 1196-1225.*
Jaakko Parkkinen and Jukka Finne; Occurrence of N-Acetylglucosamine 6-Phosphate in Complex Carbohydrates; The Journal of Biological Chemistry; Sep. 15, 1985; pp. 10971-10975; vol. 260, No. 20 issue; The American Society of Biological Chemists, Inc.; USA.

(Continued)

*Primary Examiner* — Chris R Tate
*Assistant Examiner* — Douglas F White
(74) *Attorney, Agent, or Firm* — Zarley Law Firm, P.L.C.

(57) ABSTRACT

A method of testing for discerning substitution of carbohydrate ester includes the step of providing a predetermined amount of a solution. Further, the method also includes adding ammonium hydroxide and sodium borohydride to the solution. The method also includes the step of transferring the solution to an ammonium ion exchange cartridge and collecting the eluate from the cartridge. Also included in the method is the step of analyzing the sample in a mass spectrometer to produce a mass spectrum. Further, the method includes calculating the amu of phosphate and sulfate substitution of the ion and comparing it to the actual amu of the found ion.

9 Claims, 12 Drawing Sheets

(56) References Cited

OTHER PUBLICATIONS

Rudiger W. Veh, Jean-Claude Michalski, Anthony P. Corfield, Michael Sander-Wewer, Dagmar Gies, and Roland Schauer; New Chromatographic System for the Rapid Analysis and Preparation of Colostrum Sialyloligosaccharides; Journal of Chromatography; 1981; pp. 313-322; Elsevier Scientific Publishing Company, The Netherlands.

Tadao Saito and Takatoshi Itoh; Variations and Distributions of O-Glycosidically Linked Sugar Chains in Bovine κ-Casein; Abstract; pp. 1768-1774; vol. 75; Journal of Dairy Science, Japan.

Pramod K. Gopal and H.S. Gill; Oligosaccharides and Glycoconjugates in Bovine Milk and Colostrum; British Journal of Nutrition; 2000; pp. S69-S74; vol. 84, Suppl 1; New Zealand Dairy Research Institute; New Zealand.

Harsharnjit S. Gill and M.L. Cross; Anticancer Properties of Bovine Milk; British Journal of Nutrition; 2000; pp. S161-S166; vol. 84, Suppl 1; Institute of Food, Nutrition and Human Health; New Zealand.

Fangyu Hu, Kazuo Furihata, Mie Ito-Ishida, Shuichi Kaminogawa, and Masaru Tanokura; Nondestructive Observation of Bovine Milk by NMR Spectroscopy: Analysis of Existing States of Compounds and Detection of New Compounds; Journal of Agricultural and Food Chemistry; 2004; pp. 4969-4974; vol. 52, No. 16; The University of Tokyo; Japan.

William A. Bubb, Tadasu Urashima, Kuniaki Kohso, Tadashi Nakamura, Ikichi Arai and Tadao Saito; Occurrence of an Unusual Lactose Sulfate in Dog Milk; carbohydrate research; 1999 pp. 123-128; vol. 318; Elsevier Science Ltd.; The Netherlands.

Robert E. Ward; Isolation of Milk Oligosaccharides using Solid-Phase Extraction; Open Glycoscience; 2009; 2, pp. 9-15.

Michael Messer; Identification of N-Acetyl-4-0-acetylneuraminyl-lactose in Echidna Milk; Biochem. J. (1974); 139; pp. 415-420.

Mary Beth Flanders Stepans, et al.; Early Consumption of Human Milk Oligosaccharides Is Inversely Related to Subsequent Risk of Respiratory and Enteric Disease in Infants; Breastfeeding Medicine; vol. 1, No. 4; 2006; pp. 207-215.

N. Tao et al., Bovine Milk Glycome; Journal of Dairy Science; vol. 91, 2008; pp. 3768-3778.

N. Tao et al., Variations in bovine milk oligosaccharides during early and middle lactation stages analyzed by high-performance liquid chromatography-chip/mass spectrometry; Journal of Dairy Science; vol. 92, 2009; pp. 2991-3001.

Tomaso R.I. Cataldi, et al.; Determination of mono-and disaccharides in milk and milk products by high-performance anion-exchange chromatography with pulsed amperometric detection; Analytica Chimica Acta; vol. 485; Issue 1, May 26, 2003, pp. 43-49.

\* cited by examiner

METHOD OF DISCERNING SUBSTITUTION OF CARBOHYDRATE ESTERS

CROSS REFERENCE TO RELATED APPLICATIONS

This application is a continuation in part of U.S. application Ser. No. 13/426,891, filed Mar. 22, 2012, which claims the benefit of U.S. Provisional Application No. 61/513,921, filed Aug. 1, 2011.

BACKGROUND OF THE INVENTION

This invention relates to a method of discerning esters of carbohydrates. More specifically, the present invention relates to a laboratory method that can be used to discern whether a carbohydrate ester is phosphorylated or sulfated.

When an isolated carbohydrate ester is analyzed using mass spectrometry there is no qualitative way to discern between a phosphate substitution and a sulfate substitution using mass spectrometry. This problem is due to the phosphate and sulfate esters being isobaric in a mass spectrometer.

The inability to discern between phosphate and sulfate substitution has hindered structural analysis of milk oligosaccharides. This in turn has limited the understanding of possible milk oligosaccharide's anti-cancer activities.

Using a hydride insertion reduction reaction a single hydrogen is added if a phosphate is present, thereby adding 1 amu. If a sulfate is present two hydrogens are added, thereby adding 2 amu. Since phosphorous and sulfur have 1 amu difference in atomic mass, the ions have 2 amu difference in molecular mass. This difference in molecular mass is sufficient for detection by mass spectrometers.

Thus, a principal object of the present invention is to provide a method for discerning between phosphate and sulfate substitution.

SUMMARY OF THE INVENTION

A method of testing for discerning substitution of carbohydrate ester includes the step of providing a predetermined amount of a solution. Further, the method also includes adding ammonium hydroxide and sodium borohydride to the solution. The method also includes the step of transferring the solution to an ammonium ion exchange cartridge and collecting the eluate from the cartridge. Also included in the method is the step of analyzing the sample in a mass spectrometer to produce a mass spectrum. Further, the method includes calculating the amu of phosphate and sulfate substitution of the ion and comparing it to the actual amu of the found ion.

DESCRIPTION OF THE PREFERRED EMBODIMENT

Figure 1:
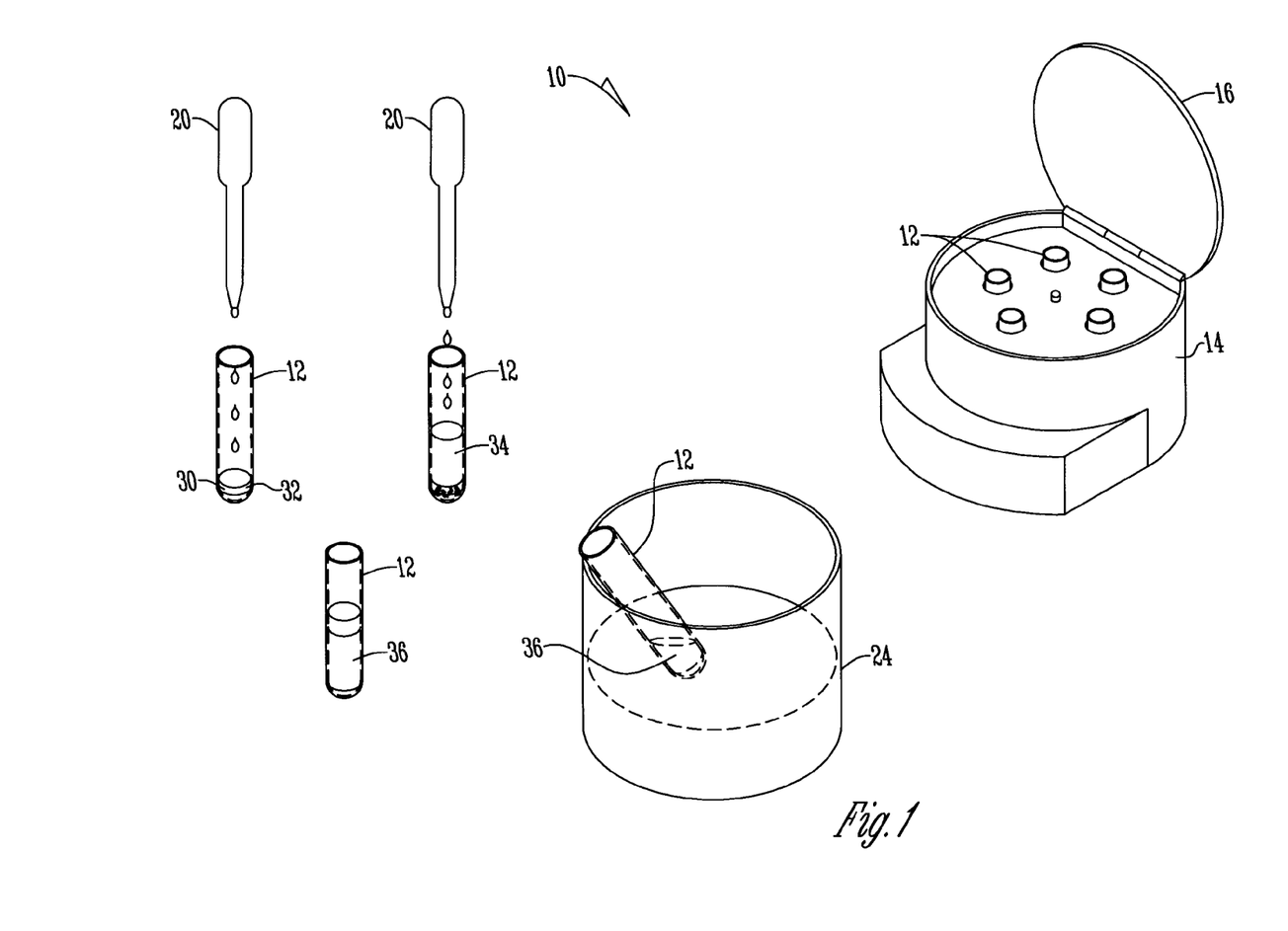
FIG. 1 is a perspective view of the system for discerning substitution of carbohydrate esters.
Figure 2:
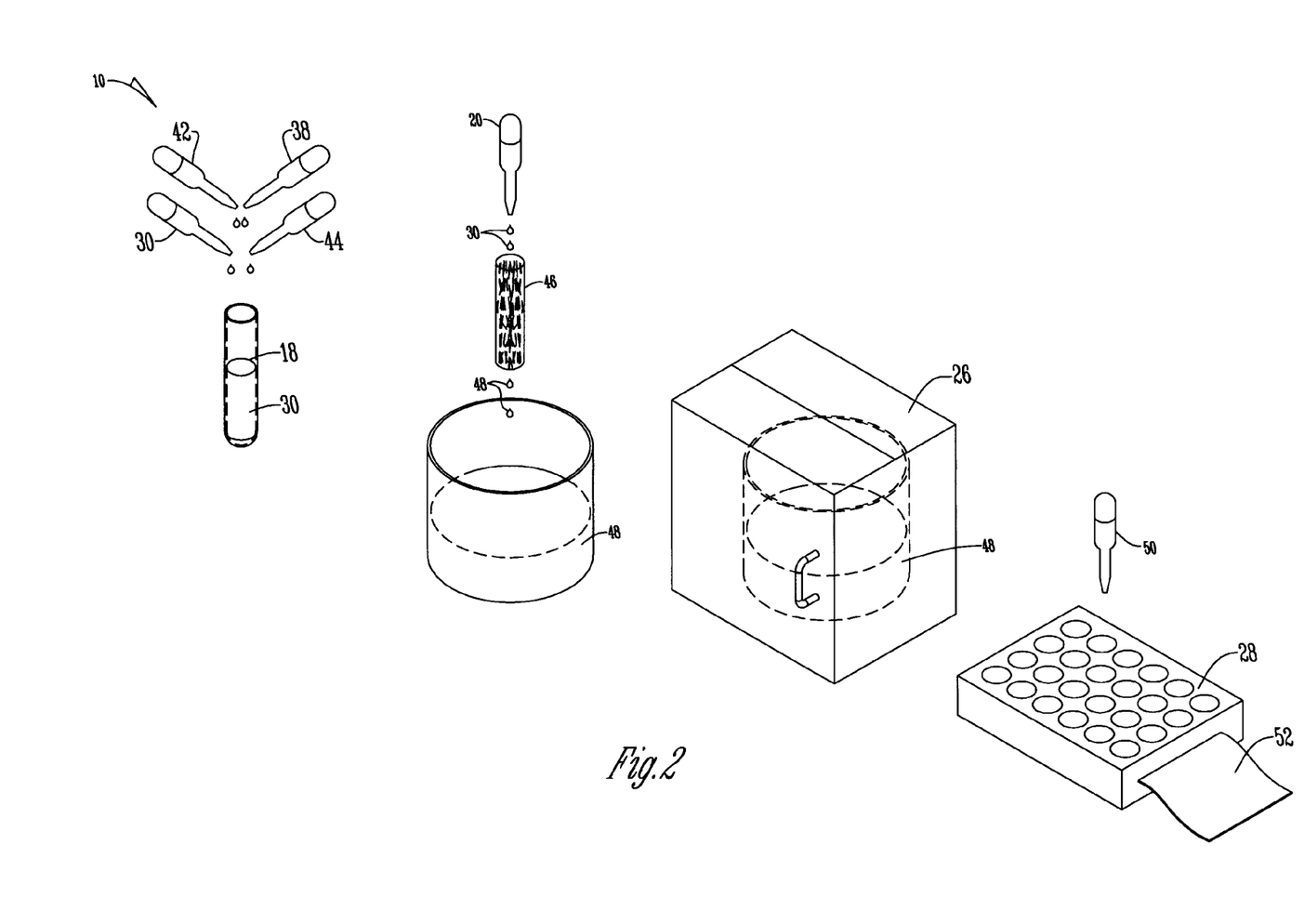
FIG. 2 is a perspective view of the system for discerning substitution of carbohydrate esters.
Figure 3:
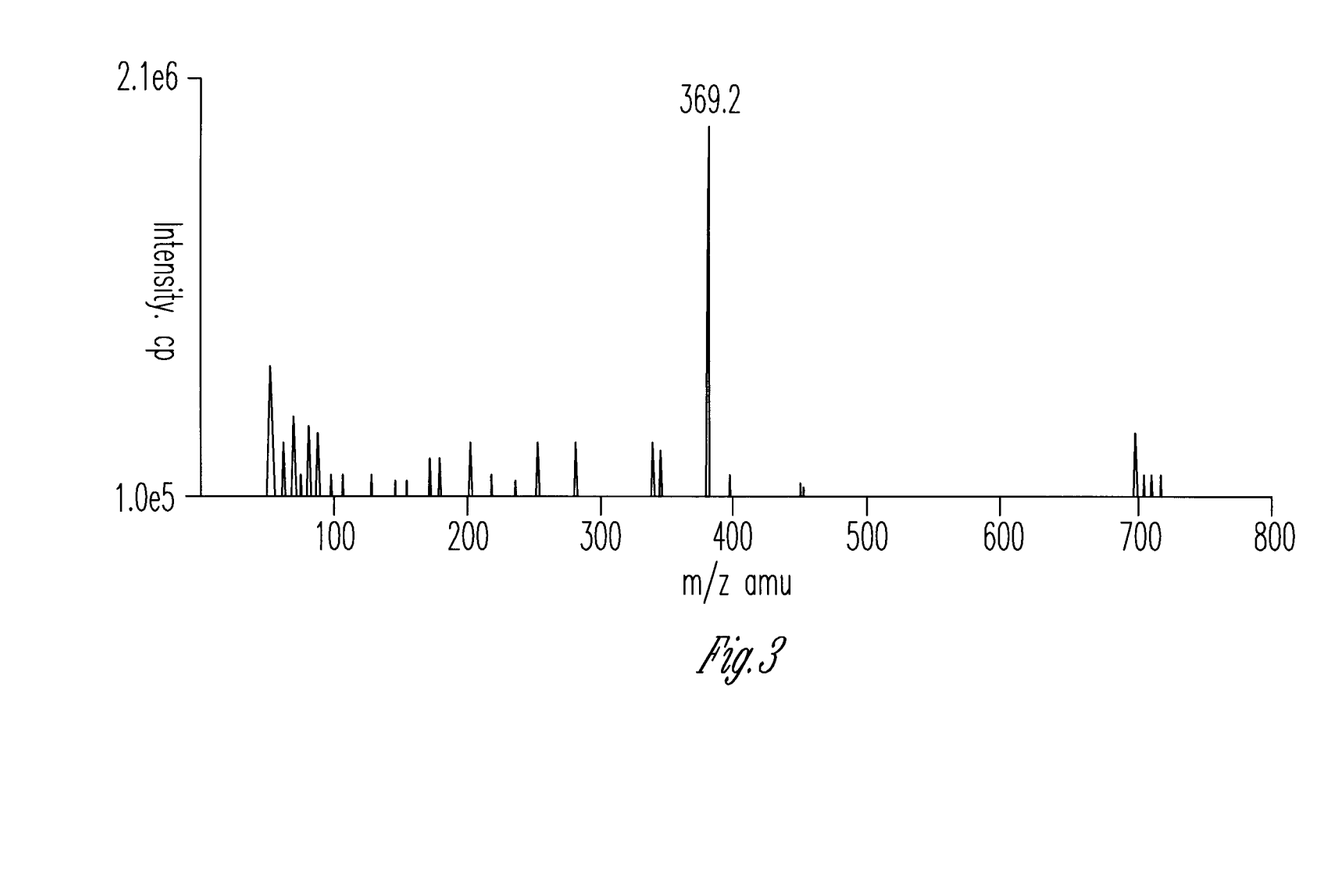
FIG. 3 is a mass spectrum of hydride inserted milk oligosaccharide.

The figures show a system 10 utilized in order to discern whether a carbohydrate ester is phosphorylated or sulfated. The system 10 includes a centrifuge tube 12, a centrifuge 14 having a cap 16 disposed thereon, a test tube 18, a plurality of pipets 20, an ion exchange cartridge 22, a plurality of beakers 24. In addition the system can include a freezer 26 and a mass spectrometer 28.

The method used to discern whether a carbohydrate ester is phosphorylated or sulfated using the system 10 is to pipet a predetermined amount, preferably between 0.1 mL and 1.0 mL, of a solution 30 into the test tube 18.

In one embodiment the solution 30 is cold fat free milk 32 that undergoes the following treatment. In this embodiment a predetermined amount of fat free milk 32 is pipetted into a centrifuge tube 12. In one embodiment 0.1 mL of fat free milk 32 is pipetted into the centrifuge tube 12. Next, ethanol 34 is added to the centrifuge tube 12. In one embodiment 1.0 mL of cold 95% ethanol 34 is added. The centrifuge tube 14 i2 placed in a centrifuge 14. The cap 16 of the centrifuge 14 is then closed and the centrifuge tube 12 is centrifuged for a predetermined amount of time, in one embodiment between 30 to 40 seconds.

During centrifuging a supernatant 36 is formed and is placed in a test tube 18. The supernatant 36 is then dried with a stream of nitrogen and water 38 is added. The solution 30 is then placed in a freezer 26 for storage until thawed for analysis.

In another embodiment the solution 30 is milk 32 that is passed through an ion exchange resin 40 (not shown). In one particular embodiment, 1.0 mL of milk 32 is passed through an ammonium ion cation exchange resin 40. The resulting solution 30 is then placed in a freezer 26 until thawed for further analysis. In yet another embodiment the solution 30 is a glycoprotein solution.

Once the solution 30 is thawed and ready for analysis ammonium hydroxide 42 is added to the test tube 18, preferably 1.0 mL. In one embodiment, 1N ammonium hydroxide 42 ($NH_4OH$) having a pH of 11.4 is used. Next, sodium borohydride 44 ($NaBH_4$) is added to the test tube 18, preferably 3 μL of 4N sodium borohydride 44 is added. The contents of the test tube 18 is then allowed to stand for a predetermined amount of time. In one embodiment the predetermined amount of time is 4 to 18 hours. During the predetermined time the solution 30 may bubble. After being allowed to stand the solution 30 is freeze evaporated, but not dried. The solution 30 is freeze evaporated to 0.2 mL.

Next, water 38 is added to the test tube 18. In one embodiment the water 38 added is 1.0 mL of 18 MOhm water 38. The contents of the test tube 18 is then pipetted into the ion exchange cartridge 22. In one embodiment the ion exchange cartridge 22 is an ammonium form exchange cartridge. Additional ammonium hydroxide 42 may be used to push the solution 30 through the ion exchange cartridge 22.

Once the solution 30 has pipetted into the ion exchange cartridge 22 the eluate 46 is collected in a beaker 24. Then the eluate 46 is placed in a freezer 26. Next, the eluate 46 is partially thawed. In an alternative embodiment the analysis is conducted after elution so the steps of freezing and thawing are omitted.

A sample 48 of the eluate 46 is transferred to another beaker 24. In one embodiment 0.05 mL is transferred and diluted with 1.0 mL water 38. The sample 48 is then transferred to a mass spectrometer 28. Preferably the sample is transferred to the mass spectrometer 28 within two minutes of removal from the freezer 26.

In one embodiment the mass spectrometer 28 uses atmospheric pressure ionization (API) and the mass spectrometer 28 is set to a negative ion mode. Alternatively, electrospray ionization (ESI) or any other method of ionization can be used. In one embodiment the mass spectrometer 28 is a triple quadropole but other types of mass spectrometers 28 are contemplated.

Figure 4:
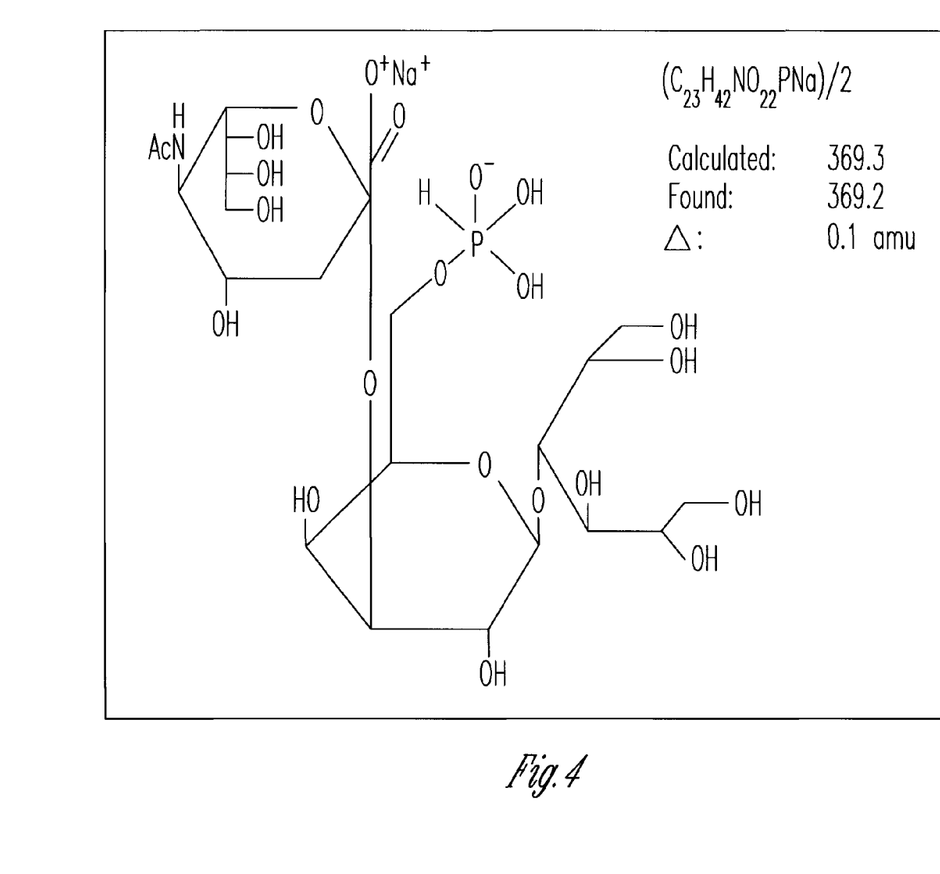
FIG. 4 is a diagram of a hypothetical ion discerned as having phosphate substitution.
Figure 5:
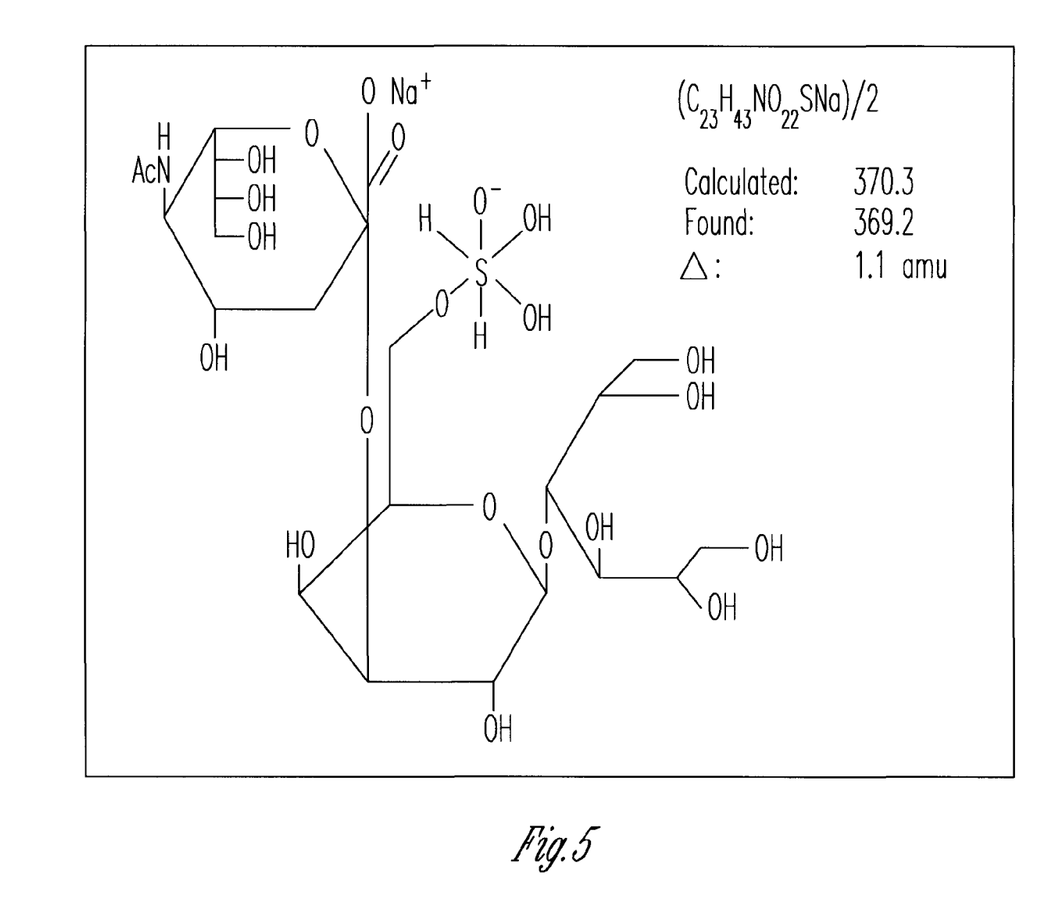
FIG. 5 is a diagram of a mass spectrum of a sample of isolated milk trisaccharide discerned as having sulfate substitution.
Figure 6:
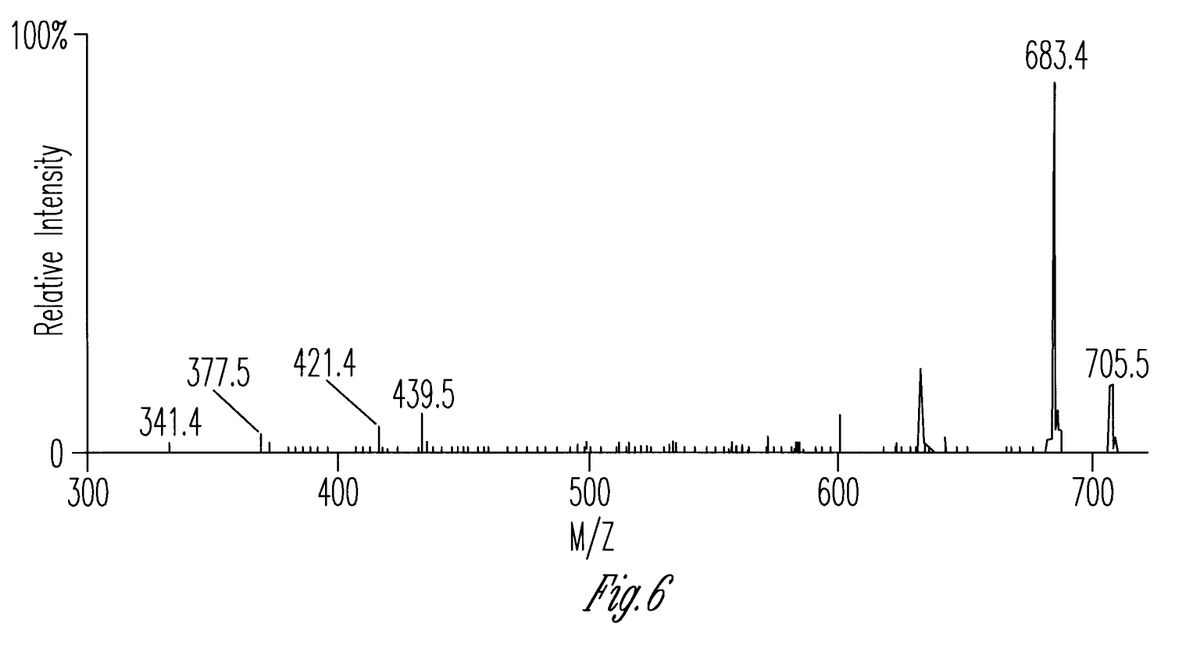
FIG. 6 is a mass spectrum with no hydride insertion reaction of milk oligosaccharide.
Figure 7:
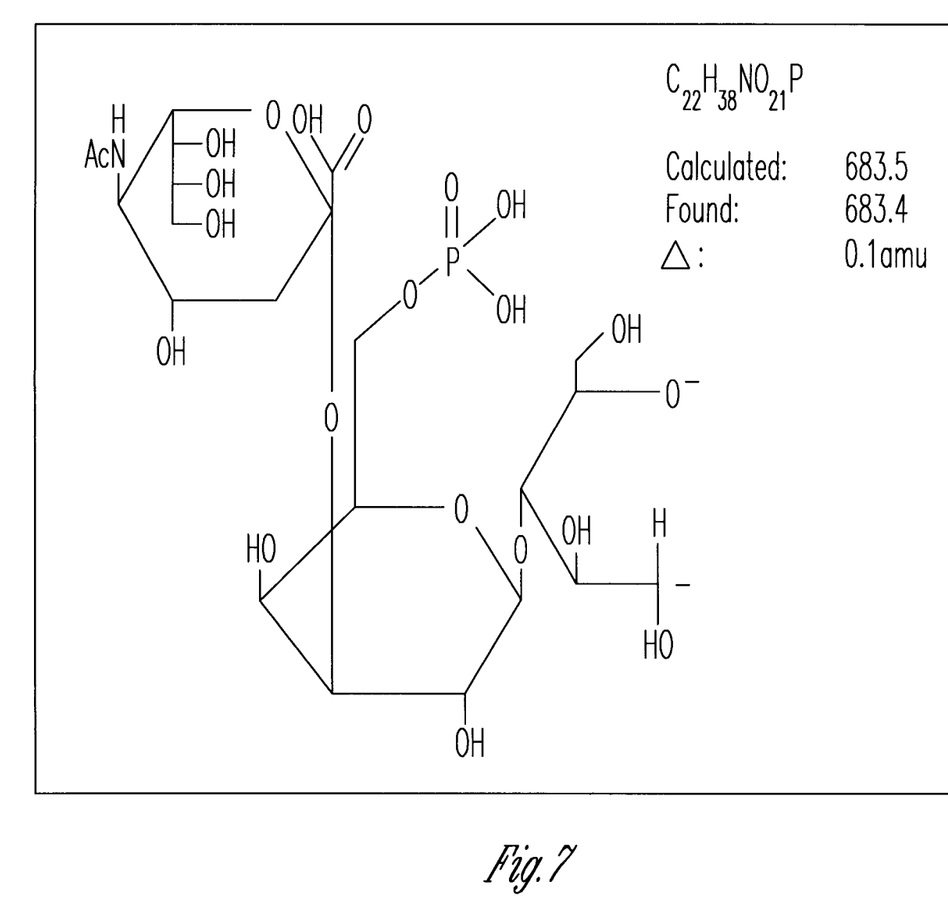
FIG. 7 is a diagram of an ion of without an inserted milk oligosaccharide.
Figure 8:
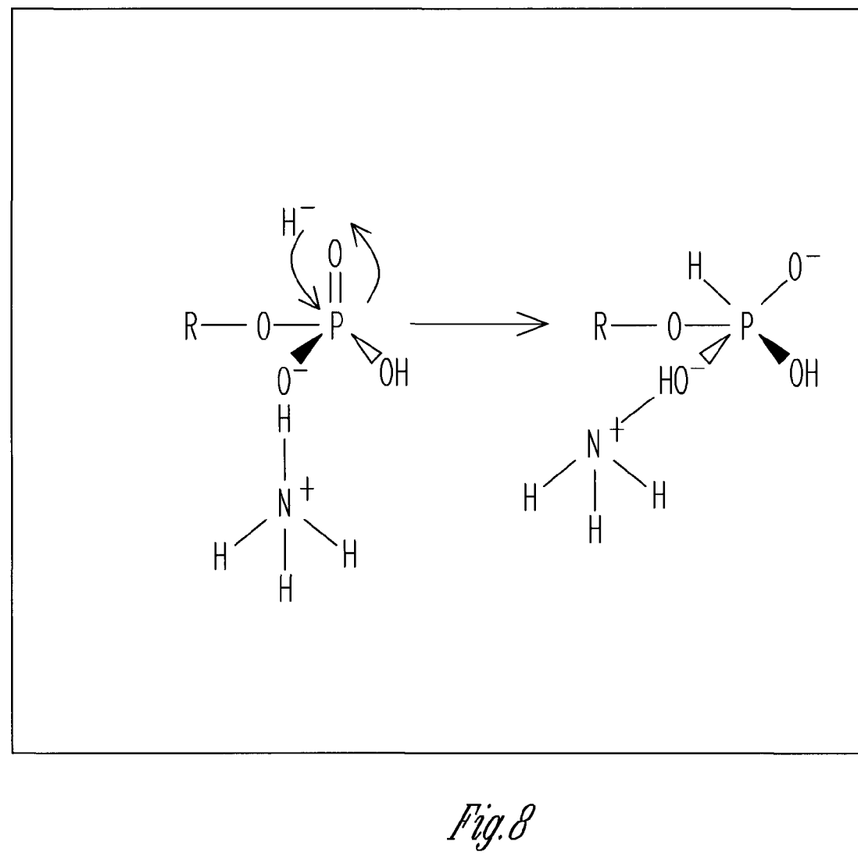
FIG. 8 is a diagram of a suggested mechanism depicting hydride insertion of a phosphate ester.
Figure 9:
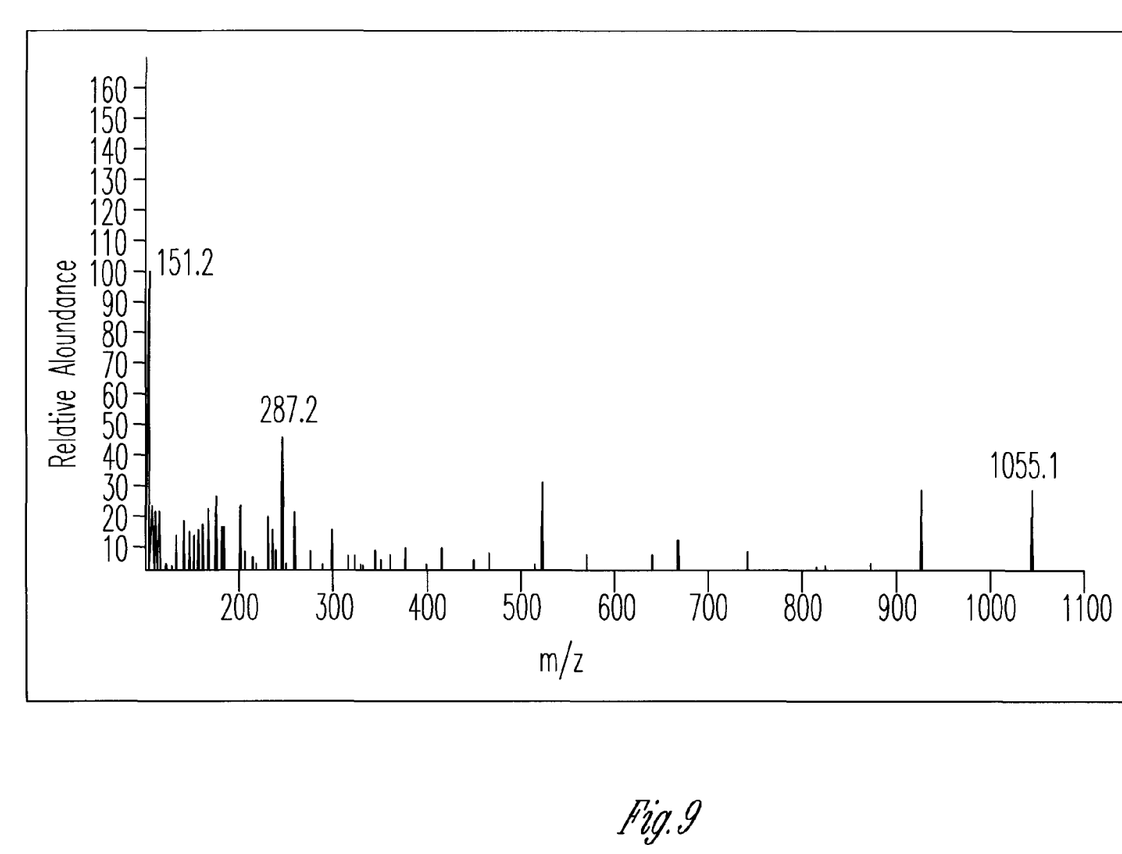
FIG. 9 is a diagram of a mass spectrum of a sample of glycoprotein discerned as having sulfate substitution.

After the sample 48 is analyzed in the mass spectrometer 28 a mass spectrum 50 is obtained. As shown in FIGS. 4 and 5, using a calculated amu for a phosphate substituted ion and a sulfate substituted ion, the difference between the calculated amu and the actual amu is determined (Δ). Using the accuracy of the mass spectrometer 28, the difference between calculated and found amu shows that the ion is either a sulfated or phosphorylated ester.

For illustration, shown in FIGS. 3 to 7, this calculation is used to determine that the major ion shown at 683.3 m/z peak of a fat free bovine milk 32 is due to phosphate substitution. In this embodiment the calculated amu for a phosphate substituted ion was 369.3 amu and the calculated amu for a sulfate substituted ion was 370.3 amu. The actual amu was 369.2. The calculated difference (Δ) between the actual amu and phosphate amu is only 0.1, whereas the sulfate amu was 1.1, indicating phosphate substitution. More specifically, the m/z peak at 683.3 is 3'-N-acetyl neuraminyl lactose 6'-phosphate.

Figure 10:
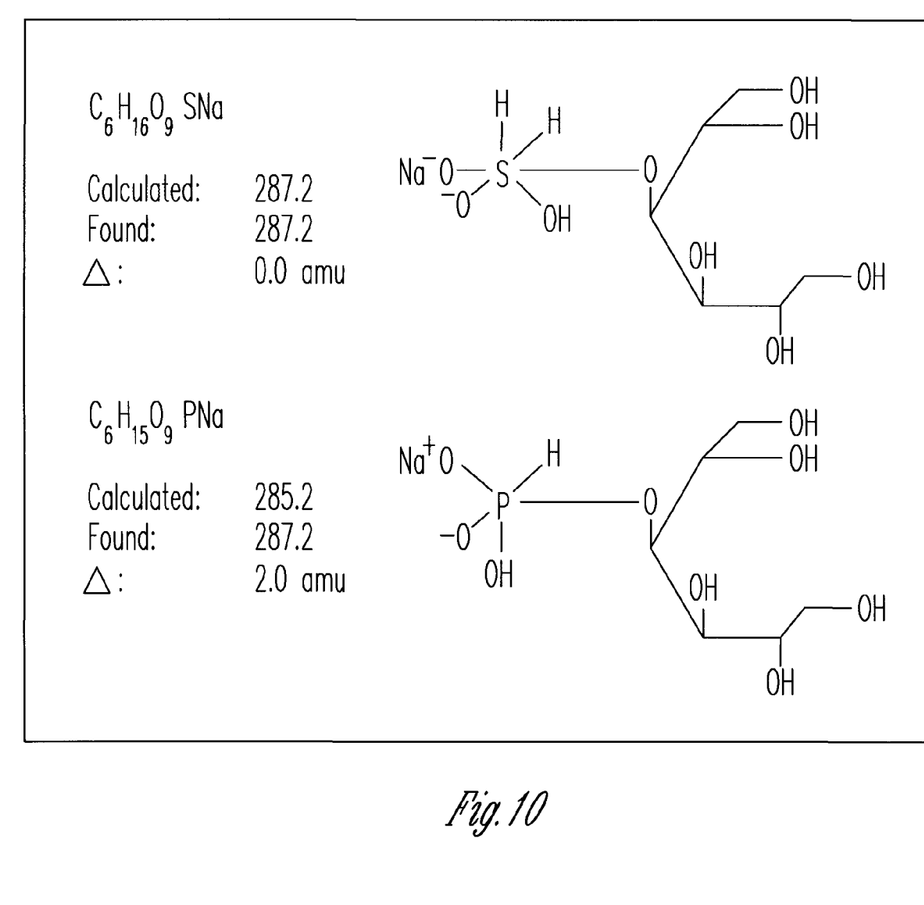
FIG. 10 is a diagram of an O-linked oligosaccharide ions having sulfate substitution and phosphate substitution.
Figure 11:
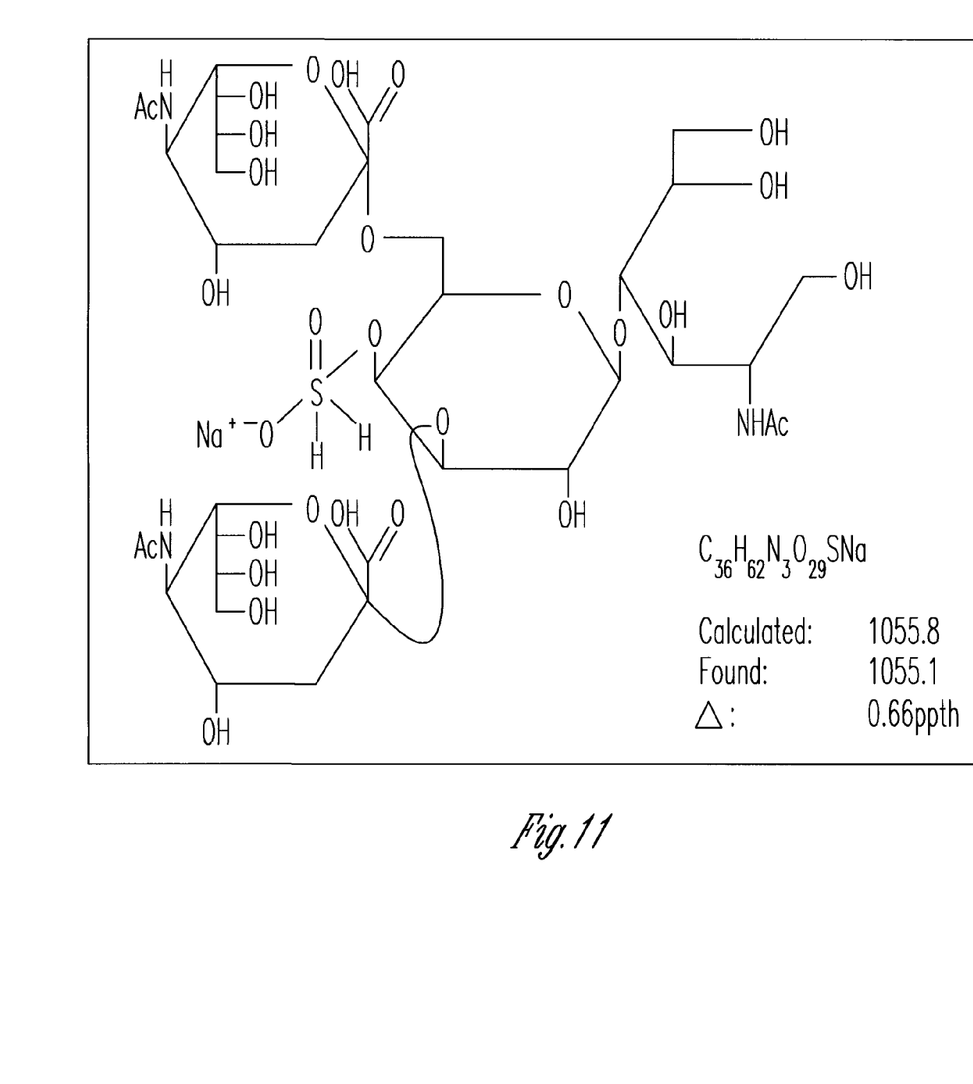
FIG. 11 is a diagram of a hypothetical O-linked oligosaccharide ion having sulfate substitution.
Figure 12:
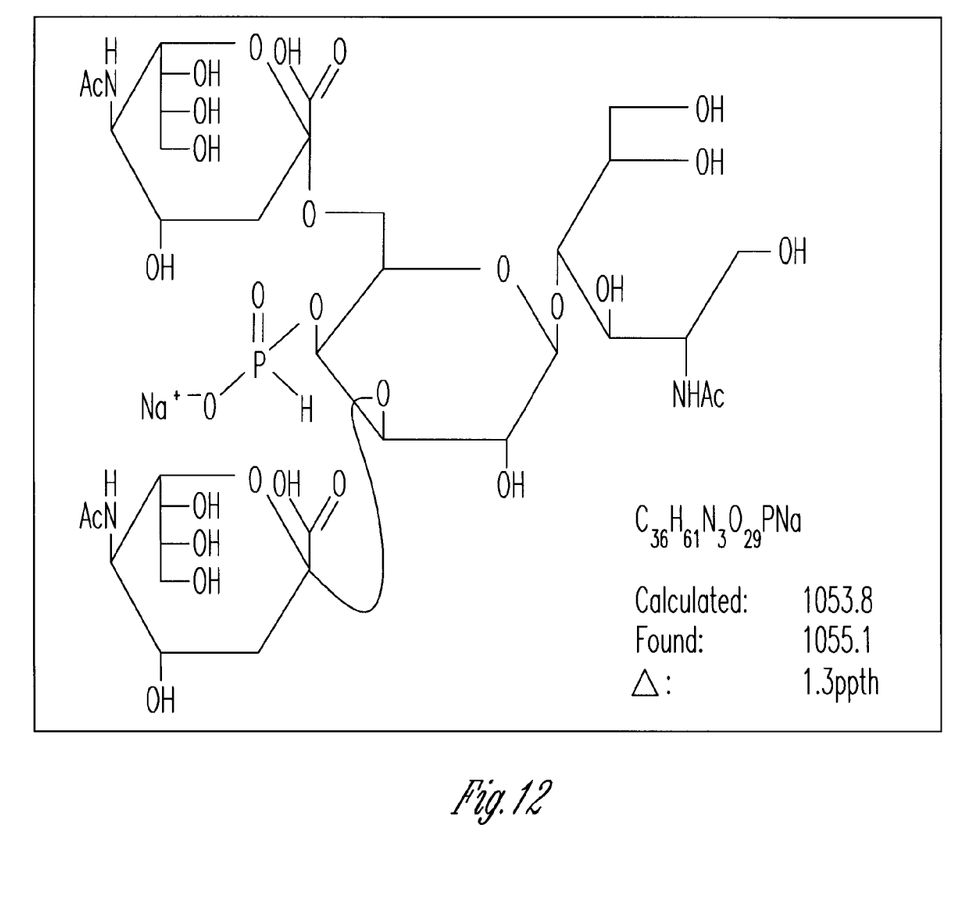
FIG. 12 is a diagram of a hypothetical O-linked oligosaccharide ion having phosphate substitution.

Similarly, an O-linked oligosaccharide bound to glycoprotein 30 is analyzed as shown in FIGS. 9 to 12. As shown in FIG. 10, the calculated difference between the sulfate substitution amu and the actual amu is 0.1, whereas the phosphate substitution difference is 2.0 amu, indicating sulfate substitution. Further, the calculated difference between the sulfate substitution in FIG. 11 is 0.66 amu, whereas the phosphate substitution as shown in FIG. 12 is 1.3 amu, indicating sulfate substitution. Thus, at least all of the stated problems have been overcome.

What is claimed is:

1. A method of discerning substitution of carbohydrate esters comprising the steps of:
   providing a predetermined amount of a solution containing carbohydrate esters;
   adding ammonium hydroxide and sodium borohydride to the solution and letting the solution stand for a predetermined amount of time;
   transferring the solution to an ion exchange cartridge;
   collecting an eluate from the ion exchange cartridge; and
   running a sample of the eluate in a mass spectrometer to produce a mass spectrum so as to discern the substitution.

2. The method of claim 1 further comprising the steps of calculating an amu for a reference ion based on sulfate substitution and phosphate substitution, and comparing the amu of the reference ion to the amu of a substituted ion of the eluate as produced from the mass spectrum.

3. The method of claim 1 wherein the solution is fat free milk.

4. The method of claim 1 wherein the solution is a glycoprotein solution.

5. The method of claim 1 wherein the ion exchange cartridge is an ammonium form ion exchange cartridge.

6. The method of claim 1 wherein 1.0 mL of 1N ammonium hydroxide having a pH of 11.4 is used.

7. The method of claim 1 where 3 μL of 4N sodium borohydride is used.

8. The method of claim 1 wherein the predetermined amount of time is between 4 and 18 hours.

9. The method of claim 1 further comprising the step of freezing the eluate before analyzing.

* * * * *